United States Patent
Panescu et al.

(10) Patent No.: US 7,364,546 B2
(45) Date of Patent: *Apr. 29, 2008

(54) MULTI-FUNCTIONAL MEDICAL CATHETER AND METHODS OF USE

(75) Inventors: Dorin Panescu, San Jose, CA (US); David K. Swanson, Campbell, CA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/687,832

(22) Filed: Mar. 19, 2007

(65) Prior Publication Data

US 2007/0156048 A1 Jul. 5, 2007

Related U.S. Application Data

(63) Continuation of application No. 10/428,308, filed on May 2, 2003, now Pat. No. 7,194,294, which is a continuation-in-part of application No. 10/305,256, filed on Nov. 25, 2002, now Pat. No. 6,824,515, which is a continuation of application No. 09/750,439, filed on Dec. 28, 2000, now Pat. No. 6,508,765, which is a continuation of application No. 09/227,281, filed on Jan. 6, 1999, now Pat. No. 6,206,831.

(51) Int. Cl.
*A61B 18/00* (2006.01)
*A18B 18/14* (2006.01)

(52) U.S. Cl. .............. 600/439; 600/467; 601/2; 606/41; 607/99

(58) Field of Classification Search ............ 606/41; 600/439, 476; 601/2; 607/99

See application file for complete search history.

(56) References Cited

U.S. PATENT DOCUMENTS

| | | | |
|---|---|---|---|
| 4,706,681 A | * | 11/1987 | Breyer et al. ............ 600/374 |
| 4,917,097 A | | 4/1990 | Proudian et al. |
| 4,998,933 A | | 3/1991 | Eggers et al. |
| 5,178,620 A | | 1/1993 | Eggers et al. |
| 5,228,442 A | * | 7/1993 | Imran ...................... 600/374 |
| 5,295,484 A | | 3/1994 | Marcus et al. |
| 5,385,148 A | | 1/1995 | Lesh et al. |
| 5,409,000 A | | 4/1995 | Imran |

(Continued)

FOREIGN PATENT DOCUMENTS

EP 0499491 A2 8/1992

(Continued)

*Primary Examiner*—Lee S. Cohen
(74) *Attorney, Agent, or Firm*—Orrick Herrington & Sutcliffe LLP (57) ABSTRACT

The present invention provides multi-functional medical catheters, systems and methods for their use. In one particular embodiment, a medical catheter (100) includes a flexible elongate body (105) having a proximal end (110) and a distal end (120). A plurality of spaced apart electrodes (130-136) are operably attached to the flexible body near the distal end. At least some of the electrodes are adapted for mapping a tissue and, in some embodiments, at least one of the electrodes is adapted for ablating a desired portion of the tissue. The catheter includes a plurality of tissue orientation detectors (140-146) disposed between at least some of the electrodes. In this manner, the medical catheter is capable of tissue mapping, tissue imaging, tissue orientation, and/or tissue treatment functions.

17 Claims, 10 Drawing Sheets

U.S. PATENT DOCUMENTS

| | | | |
|---|---|---|---|
| 5,419,767 A | 5/1995 | Eggers et al. | |
| 5,456,259 A | 10/1995 | Barlow et al. | |
| 5,487,391 A | 1/1996 | Panescu | |
| 5,571,088 A | 11/1996 | Lennox et al. | |
| 5,590,659 A | 1/1997 | Hamilton et al. | |
| 5,598,848 A | 2/1997 | Swanson et al. | |
| 5,606,975 A | 3/1997 | Liang et al. | |
| 5,630,837 A * | 5/1997 | Crowley | 601/2 |
| 5,640,371 A | 6/1997 | Schmidt et al. | |
| 5,643,197 A | 7/1997 | Brucker et al. | |
| 5,697,281 A | 12/1997 | Eggers et al. | |
| 5,697,536 A | 12/1997 | Eggers et al. | |
| 5,697,882 A | 12/1997 | Eggers et al. | |
| 5,697,909 A | 12/1997 | Eggers et al. | |
| 5,713,363 A | 2/1998 | Seward et al. | |
| 5,735,280 A | 4/1998 | Sherman et al. | |
| 5,749,833 A | 5/1998 | Hakki et al. | |
| 5,752,518 A | 5/1998 | McGee et al. | |
| 5,769,847 A | 6/1998 | Panescu et al. | |
| 5,840,030 A * | 11/1998 | Ferek-Petric et al. | 600/439 |
| 5,846,204 A | 12/1998 | Solomon | |
| 5,882,346 A | 3/1999 | Pomeranz et al. | |
| 5,954,649 A | 9/1999 | Chia et al. | |
| 6,053,868 A | 4/2000 | Geistart et al. | |
| 6,206,831 B1 * | 3/2001 | Suorsa et al. | 600/439 |
| 6,240,307 B1 | 5/2001 | Beatty et al. | |
| 6,490,474 B1 | 12/2002 | Willis et al. | |
| 6,516,807 B1 | 2/2003 | Panescu et al. | |
| 6,922,579 B2 | 7/2005 | Taimisto et al. | |
| 2002/0068867 A1 | 6/2002 | Ameling et al. | |

FOREIGN PATENT DOCUMENTS

| | | |
|---|---|---|
| EP | 0928601 A1 | 7/1999 |
| WO | WO 96/00036 | 1/1996 |
| WO | WO 98/29032 | 7/1998 |

* cited by examiner

MULTI-FUNCTIONAL MEDICAL CATHETER AND METHODS OF USE

CROSS REFERENCE TO RELATED APPLICATIONS

This application is a continuation of U.S. application Ser. No. 10/428,308, entitled "Multi-Functional Medical Catheter and Methods of Use," filed May 2, 2003, now U.S. Pat. No. 7,194,294 which is a continuation-in-part of U.S. application Ser. No. 10/305,256, filed on Nov. 25, 2002, now U.S. Pat. No. 6,824,525 which is a continuation of U.S. application Ser. No. 09/750,439, filed on Dec. 28, 2000, now U.S. Pat. No. 6,508,765, which is a continuation of U.S. application Ser. No. 09/227,281, filed on Jan. 6, 1999, now U.S. Pat. No. 6,206,831, all of which are incorporated herein by reference.

BACKGROUND OF THE INVENTION

The invention relates generally to the field of medical catheters, and in particular, to multi-functional medical catheters adapted to map, orient and/or provide treatment for a variety of medical conditions.

Physicians make use of catheters today in medical procedures that are best performed by gaining access into interior regions of the body. For example, in electrophysiological therapy, ablation is used to treat cardiac rhythm disturbances. Such a therapy may be used, for instance, to treat atrial fibrillation by forming lesions in heart tissue at desired locations to interrupt undesirable electrical pathways.

During these procedures, the physician typically first maps the electrical activity of the patient's heart to help determine the location of any abnormalities. The physician then steers a catheter through a main vein or artery into the interior region of the heart that is to be treated. An ablation element carried on the distal end of the catheter is positioned near the tissue that is to be ablated. For such treatments, the delivery of ablating energy must be closely governed to avoid incidence of tissue damage and coagulum formation. Further, the ablation catheters must be precisely positioned adjacent to and preferably in contact with the tissue to be treated, to insure the lesions are properly located.

Physicians and staff performing diagnostic and therapeutic procedures, such as electrophysiological therapy, typically require an imaging system to assist them in positioning the ablation catheter. Mini-transesophageal echocardiography (mini-TEE) probes are available, however, these probes must be swallowed or inserted down the patient's throat. Such probes are poorly tolerated by patients unless they are fully anesthetized. Further, these probes can be rather large (i.e., 20 French in diameter), use complex transducer configurations and may have difficulty in detecting tissue contact by the ablation elements. Further, the mapping, imaging and treatment often requires multiple instruments or catheters, involving complex procedures as well as the introduction or reintroduction of multiple catheters into the patient. Improvements are desired.

BRIEF SUMMARY OF THE INVENTION

The present invention provides multi-functional medical catheters, systems and methods for their use. In some embodiments, the catheters include ultrasound-guided ablation catheters. Catheters and systems of the present invention will be particularly useful for precise positioning of ablation catheters prior to ablation of cardiac tissue, such as that required for the treatment of atrial fibrillation. Further, the functionality of some of the embodiments permits a single catheter to be used for tissue mapping, tissue orientation, tissue imaging, and/or tissue treatment, including ablation. Some of the systems of the present invention use transducers in the distal end of the catheter to assist the operator in determining whether or not the ablation elements are in contact with the tissue to be ablated. Non-ablation catheters also fall within the scope of the present invention, with such catheters providing tissue mapping, tissue orientation and/or tissue imaging functions.

In one particular embodiment, a medical catheter of the present invention includes a flexible elongate body having a proximal end and a distal end. A plurality of spaced apart electrodes are operably attached to the flexible body near the distal end. At least some of the electrodes are adapted for mapping a tissue. The catheter includes a plurality of tissue orientation detectors disposed between at least some of the electrodes. In this manner, the medical catheter is capable of both tissue mapping and tissue orientation functions. In some embodiments, at least one of the electrodes is adapted for ablating a desired portion of the tissue, with the catheter capable of tissue ablation or other treatments.

In some aspects, at least one of the electrodes is adapted for both mapping and ablation. In some aspects, the electrodes adapted for ablating have at least one tissue orientation detector adjacent thereto. In such a manner, the detector(s) help determine the location of the ablation electrode prior to ablation. For example, the detectors may operate to determine tissue contact, to detect a distance to the tissue, to detect a three-dimensional position relative to the tissue, and the like. In some aspects, at least one of the electrodes includes a tip electrode coupled to a tip of the distal end.

The tissue orientation detectors may have a variety of configurations within the scope of the present invention. For example, in one embodiment the tissue orientation detectors include a plurality of transducers. In a particular embodiment, at least some of the transducers include ultrasound transducers. Alternatively, or in addition, at least some of the transducers are electric, magnetic, or electromagnetic tracking transducers.

The present invention further provides exemplary medical catheter systems according to the present invention. In one embodiment, the system includes a medical catheter like those detailed herein, with a controller coupled to the plurality of electrodes and tissue orientation detectors. In one aspect, the controller is adapted for controlling a tissue mapping function performed by the plurality of electrodes. In a particular aspect, the tissue mapping function includes a non-contact tissue mapping function. In one aspect, the controller is further adapted for determining a tissue ablation pattern based on a result of the tissue mapping function.

In another aspect, the medical catheter system controller is adapted for receiving a plurality of signals from the tissue orientation detectors and determining an orientation of the elongate body relative to the tissue.

In some embodiments, the medical catheter system further includes a digitizing system, and/or an RF generator electrically coupled to the plurality of electrodes. The digitizing system is adapted for producing a digitized image of the tissue. These images may be based in part on the data received by the electrodes and/or the detectors. The RF generator may facilitate using one or more electrodes to ablate tissue, or the like.

The present invention further provides exemplary methods of precisely positioning a medical catheter with respect to a tissue. In one such embodiment, the method includes providing a medical catheter system, such as one of the systems detailed herein. The method further includes inserting the flexible elongate body into a patient, mapping an electrical profile of the tissue using at least some of the electrodes, and positioning the elongate body to be proximate a tissue using the tissue orientation detectors. The positioning is based at least in part on the electrical profile of the tissue.

In one aspect, the method further includes activating at least one of the electrodes to ablate a desired region of the tissue if the controller determines that at least one of the tissue orientation detectors is in contact with the desired region. In particular aspects, at least one of the electrodes is activated to ablate a desired region of the tissue if the controller determines that one of the tissue orientation detectors located adjacent the electrode is in contact with the desired region, if the tissue orientation detector located directly proximal of the electrode is in contact with the tissue, and/or if the tissue orientation detectors closest to the electrode in both the proximal and distal directions are in contact with the tissue. In this manner, tissue contact may be determined prior to ablation.

In one aspect, methods of the present invention further include identifying a desired region of the tissue to be treated based on the electrical profile of the tissue. As discussed herein, the mapping may include a non-contact mapping in some embodiments to obtain or help obtain the electrical profile.

In another method of precisely positioning a catheter within a patient according to the present invention, the catheter is inserted into the patient. The method then includes mapping a tissue of the patient, using at least some of the plurality of spaced apart electrodes, to produce a tissue profile. The tissue profile may include, for example, a map or other depiction of a plurality of electrical pathways in the tissue. A tissue region to be treated is identified by using, at least in part, the tissue profile. The elongate body is positioned using the transducers so that at least one of the electrodes is proximate the tissue region. In one aspect, the elongate body positioning includes a three-dimensional localization positioning. The electrode(s) may be further operated to ablate the tissue region where desired to provide treatment to the patient.

In another embodiment of the present invention, a method of diagnosing and treating cardiac rhythm disturbances includes inserting a catheter into a patient, and mapping a tissue of the patient, using at least some of the plurality of spaced apart electrodes, to produce a tissue profile. The method includes identifying a tissue to be treated using the tissue profile, positioning the elongate body using the tissue orientation detectors so that at least one of the electrodes is proximate the tissue to be treated, and treating the tissue using the catheter. The treatment may include ablating the tissue using at least one electrode. Ablation may occur through the use of RF ablation, through ultrasound ablation, or the like. An exemplary description of acoustic ablation using transducer elements is described in U.S. Pat. No. 5,630,837, the complete disclosure of which is hereby incorporated by reference for all purposes. It will be appreciated by those skilled in the art that other ablation elements may be used within the scope of the present invention.

Other features and advantages of the invention will appear from the following description in which the preferred embodiment has been set forth in detail in conjunction with the accompanying drawings.

DETAILED DESCRIPTION OF THE INVENTION

Figure 1:
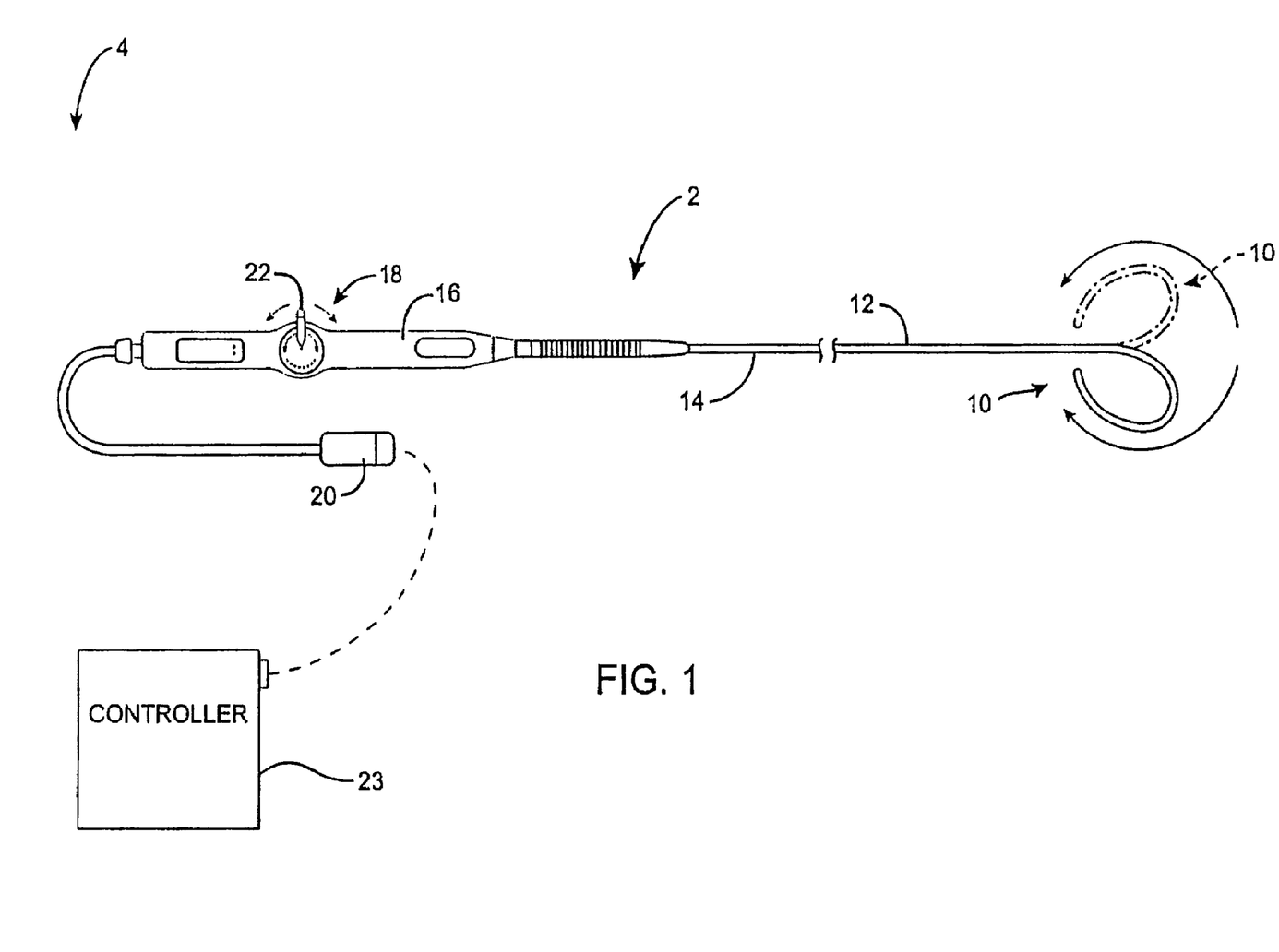
FIG. 1 depicts an overall view of a system for ablating tissue according to an embodiment of the present invention.

FIG. 1 depicts a medical catheter apparatus 2 as part of a catheter system 4 according to an embodiment of the present invention. Apparatus 2 comprises a flexible elongate body 12 having a distal end 10 and a proximal end 14. Proximal end 14 includes a handle 16 containing a steering mechanism 18. Steering mechanism 18 includes a steering lever 22 which operates a cam wheel (not shown) to maneuver flexible distal end 10 as shown by the arrows in FIG. 1. System 4 includes a connector 20 which connects with a controller 23 for operation of apparatus 2 as further described below. Controller 23 is capable of providing electrical input to apparatus 2 as needed to map, image, orient, and/or ablate a patient tissue. It will be appreciated by those skilled in the art that steering mechanism 18 can vary from that shown in FIG. 1 within the scope of the present invention. Exemplary steering mechanisms are described in International Application No. PCT/US94/11748, the complete disclosure of which is incorporated herein by reference for all purposes.

Medical catheter apparatus 2 depicted in FIG. 1 will be particularly useful in the treatment of atrial fibrillation by positioning distal end 10 within a desired region of the heart. To enter the right atrium, the physician can direct elongate body 12 through a conventional vascular introducer through the femoral vein. For entry into the left atrium, the physician can direct elongate body 12 through a conventional vascular introducer retrograde through the aortic and mitral valves. For the treatment of atrial fibrillation, it is believed that formation of lesions in the heart muscle tissue is required.

Catheters of the present invention may be used, in some embodiments, to ablate heart tissue containing abnormal electrical pathways, such as arrhythmogenic foci. Further details of apparatus 2 are shown in FIGS. 2 and 3.

Figure 2:
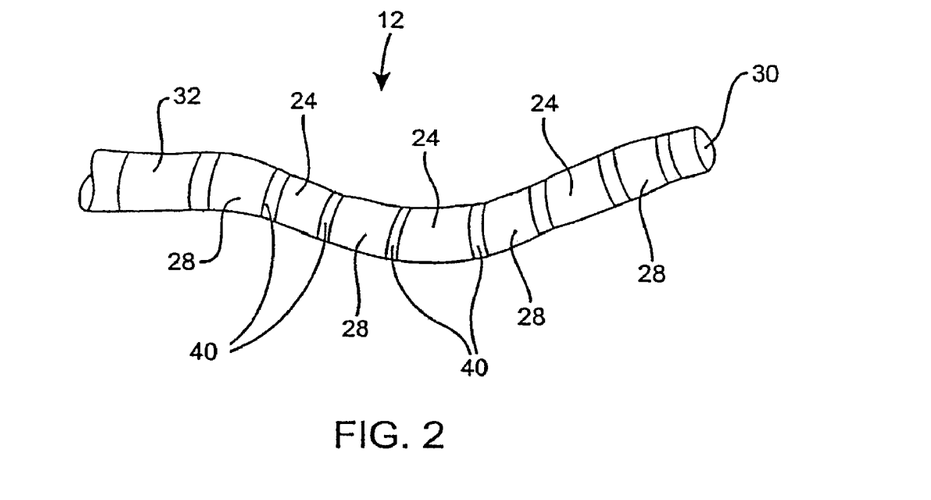
FIG. 2 depicts the distal end of a flexible elongate body as part of a catheter system according to an embodiment of the present invention.
Figure 3:
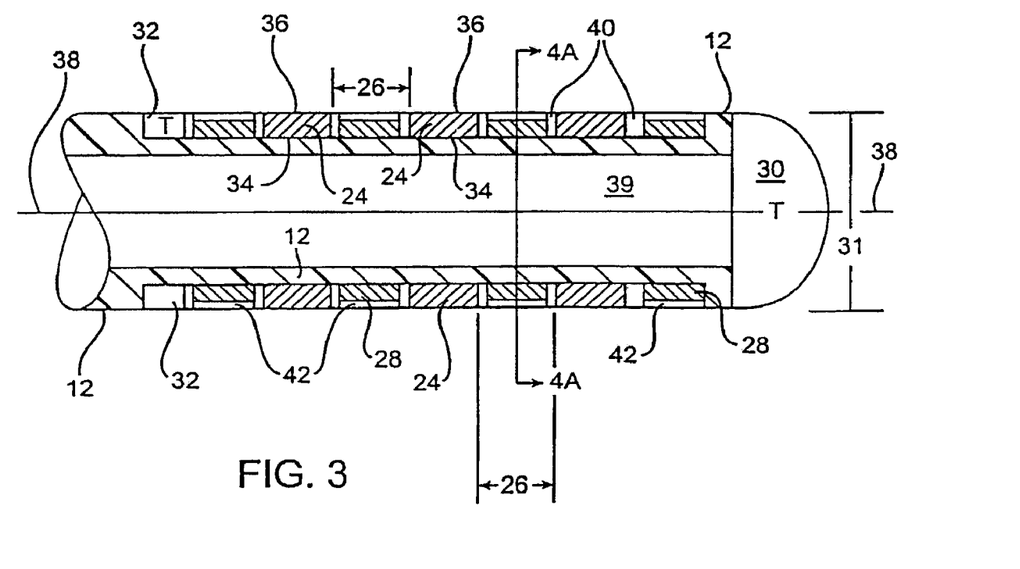
FIG. 3 depicts a cross-sectional side view of the flexible elongate body shown in FIG. 2.

FIGS. 2 and 3 depict elongate body 12 having a plurality of spaced-apart ablation elements 24, each separated by a gap 26 from adjacent ablation elements 24. Interspaced amongst ablation elements 24 are a plurality of transducer elements 28. In one embodiment, ablation elements 24 and transducer elements 28 are operably attached to body 12 in an alternating fashion. Apparatus 2 preferably includes between about two (2) and about fourteen (14) ablation elements, and between about three (3) and about fifteen (15) transducer elements. More preferably, apparatus 2 has at least one more transducer element 28 than ablation elements 24. In one embodiment, a temperature sensor 30 is provided at or near distal end 10 and a proximal temperature sensor 32 is provided proximal to ablation elements 24. Temperature sensors 30 and 32 preferably comprise thermocouples. Temperature sensors 30 and 32 also may comprise thermistors and the like within the scope of the present invention. Temperature sensors or thermocouples 30 and 32 operate to detect the temperature in the region of ablation. A plurality of insulators 40 are provided between transducer elements 28 and ablation elements 24. Insulators 40 may comprise polyimide, polyesters, teflon or the like to insulate transducer elements 28 from ablation elements 24.

Figure 4A:
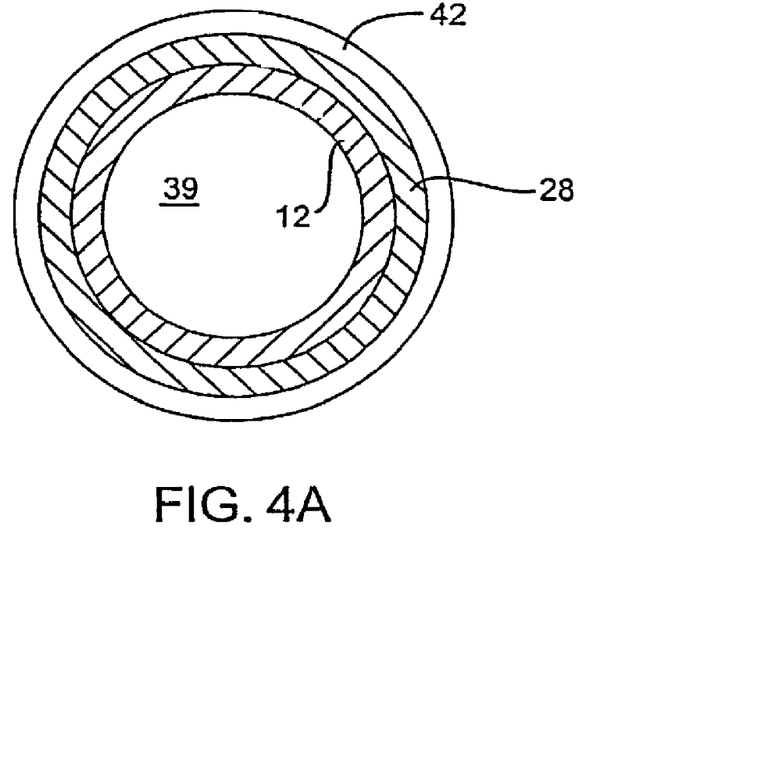
FIG. 4A depicts a cross-sectional end view of the flexible body shown in FIG. 3 taken along line 4A-4A.
Figure 4B:
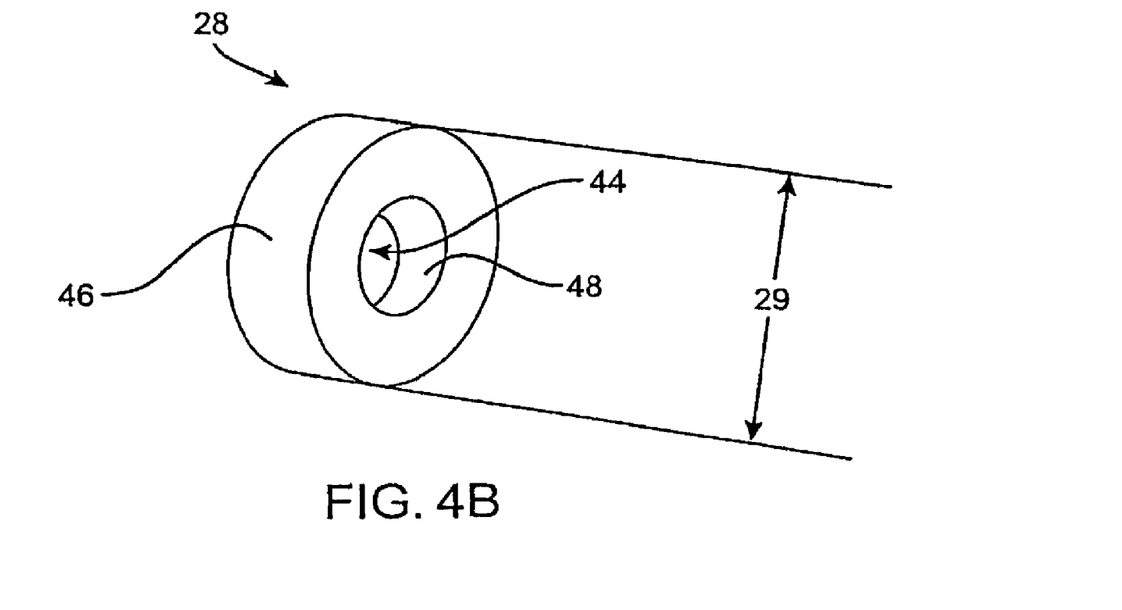
FIG. 4B depicts an overall view of a cylindrical transducer element as part of a catheter apparatus according to an embodiment of the present invention.

In one embodiment, transducer elements 28 comprise cylindrical transducer elements as best shown in FIGS. 4A-4B. Transducer elements 28 include an outer face 46 and an inner face 48. Inner faces 48 of transducer elements 28 are positioned such that a longitudinal axis 38 of body 12 passes through a throughhole 44 of each transducer element 28. In such a manner, transducer elements 28 are configured to expose outer faces 46 to surrounding tissue and fluid within the patient. In this manner, transducer elements 28 may operate to image within a three-hundred and sixty degree (360.degree.) plane that is generally perpendicular to longitudinal axis 38 without the need to rotate body 12 or transducers 28. It will be appreciated by those skilled in the art that other transducer shapes may be used within the scope of the present invention. For example, transducer elements 28 may comprise rectangular or elliptical transducer elements operably attached to distal end 10.

Transducer elements 28 may comprise ultrasound transducers. In this embodiment, transducer elements 28 may comprise piezocomposite materials, piezoceramics (such as PZT), piezoplastics, and the like. Alternatively, as further detailed below, transducer elements 28 may be adapted to transduce between a magnetic field and a voltage. Other transducer types also may be used within the scope of the present invention, including without limitation, electric, magnetic, electromagnetic, permanent magnets, wireless, optical, and the like.

In the embodiment shown in FIG. 3, transducers 28 comprise ultrasound transducer elements 28. Transducers 28 each may include a matching layer 42, or multiple matching layers 42, operably attached to the outer face 46 of each transducer element 28. Matching layers 42 operate to improve transducer element 28 performance. Transducer elements 28 also can operate without matching layers 42 within the scope of the present invention.

Transducer elements 28 have an outer diameter 29. Outer diameter 29 can be less than an outer diameter 31 of flexible elongate body 12 or, alternatively, about equal to diameter 31. Preferably, diameter 31 of body 12 is less than about eight (8) French to permit the introduction of apparatus 2 into a patient's tortuous vasculature.

Gap 26 separates adjacent ablation elements 24. Gap 26 preferably is between about 1.5 mm and about 3.0 mm in width. Gap 26, however, can be larger or smaller in size and need not be of uniform size between each two adjacent ablation elements 24. Similarly, each gap 26 need not contain a transducer element 28, and gap 26 may contain more than one transducer element 28 within the scope of the present invention. However, preferably at least some gaps 26 contain transducer elements 28, and in some embodiments, each gap 26 between ablation elements 24 contains at least one transducer element 28.

Elongate body 12 preferably includes a working lumen 39 through which longitudinal axis 38 passes. As best shown in FIG. 4A, matching layer 42 extends around the outer surface of transducer element 28. Matching layer 42 is operably attached to transducer element 28, preferably using epoxy or the like. Transducer element 28 can be operably attached to elongate body 12 in a variety of manners, including by epoxy. The use of lumen 39 is best shown in FIGS. 5A and 5B which depict two alternative embodiments of apparatus 2 of the present invention.

Figure 5A:
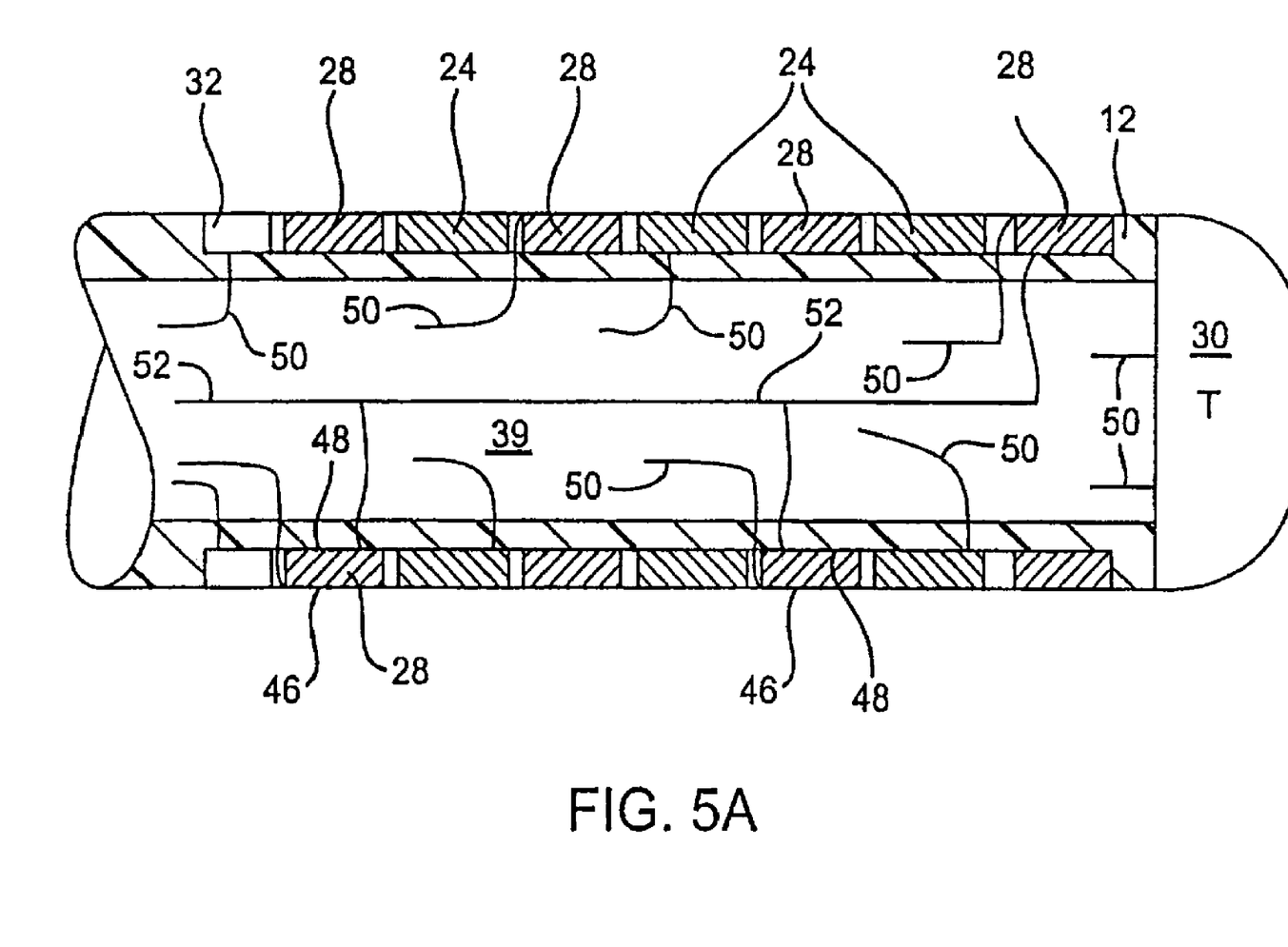
FIGS. 5A and 5B depict alternative embodiments of a medical catheter apparatus according to the present invention.

FIG. 5A depicts the medical catheter apparatus shown in FIG. 3 without matching layers 42. As can be seen in FIG. 5A, a plurality of leads 50 are operably attached to thermocouples 30 and 32, to transducer elements 28 and to ablation elements 24. For an embodiment having electrodes for ablation elements 24, each electrode has a single lead 50. Thermocouples 30 and 32 each have a pair of leads 50. Transducer elements 28 have one lead 50 in electrical communication with outer face 46. Further, a ground 52 extends from inner face 48 of transducer 28. As shown in FIG. 5A, a common ground can be used for all transducer elements 28 within a particular apparatus 2. One benefit of using a common ground 52 is that fewer leads or wires 50 are passed from distal end 10, through lumen 39 to controller 23.

Figure 5B:
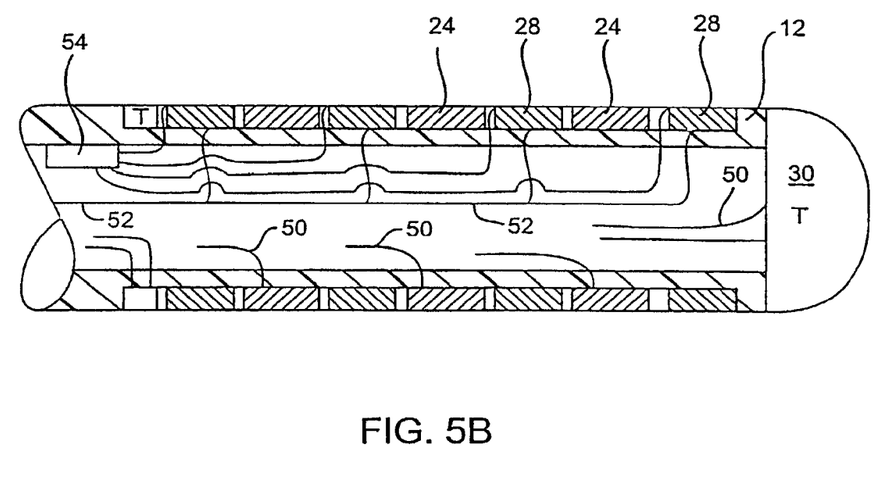

The embodiment shown in FIG. 5B depicts the use of a multiplexer 54 operably attached to distal end 10 of flexible elongate body 12. Multiplexer 54 preferably is disposed proximal of ablation elements 24 and transducer elements 28. Multiplexer 54 permits the attachment of leads 50 from transducer elements 28 to multiplexer 54 without the need to run those leads 50 to controller 23. Such a configuration can reduce the number of wires needed to be extended through lumen 39 to controller 23.

Figure 6:
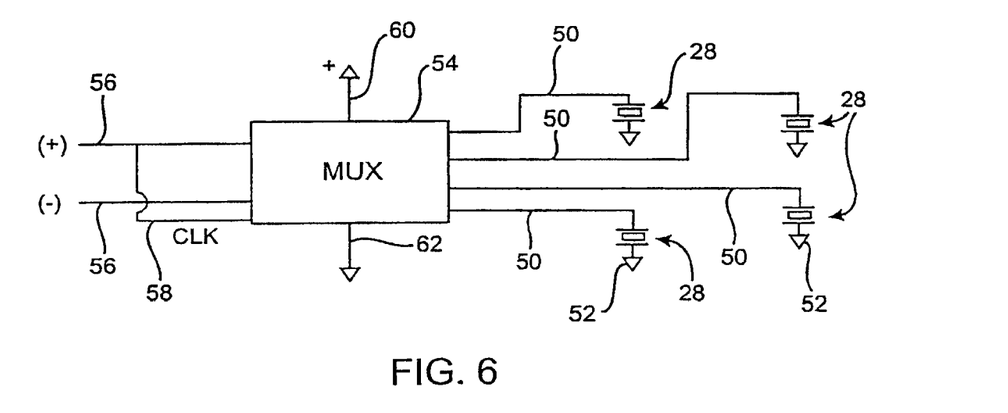
FIG. 6 depicts a schematic of a multiplexer for use with medical catheters of the present invention.

The operation of multiplexer 54 is best described in conjunction with FIG. 6. FIG. 6 depicts transducer elements 28 each having ground 52 and lead 50. Leads 50 are operably attached to multiplexer 54, preferably on the distal side of multiplexer 54. Multiplexer 54 has a ground 62 and a transmission line 60 for providing power to multiplexer circuit 54. Transmit and receive lines 56 provide a means to transmit electrical signals to multiplexer 54. Multiplexer 54 then directs electrical signals to the appropriate transducer(s) 28. Transmit/receive wires 56 carry transducer 28 excitation signals as differential pulses in series format from controller 23 to multiplexer 54. At multiplexer 54, each excitation signal is routed to an appropriate one of the transducer elements 28 in order to execute an excitation sequence used by controller 23. Similarly, return inputs or echoes received by transducer element(s) 28 are transferred to multiplexer 54 and return to controller 23 along transmit/receive lines 56.

By minimizing the number of wires required to carry the excitation signals from controller 23 to each of transducer elements 28, the diameter of elongate body 12, and more specifically, the size of lumen 39 can be reduced. Alternatively or in addition, the number of transducer elements 28 can be increased at distal end 10 without the need to require wires to be run through lumen 39 to controller 23.

Multiplexer 54 further may include a clock line 58 extending from controller 23 to multiplexer 54. Clock line 58 assists multiplexer 54 in determining which transducer element 28 is to receive an excitation signal. Alternatively, as shown in FIG. 6, clock line 58 operates by counting the number of excitation signals transmitted through transmit/receive lines 56 and incrementing a counter in multiplexer 54 to coordinate the transfer of excitation signals to the appropriate transducer 28. In one embodiment, multiplexer 54 also includes a data line (not shown in FIG. 6) extending from controller 23 to multiplexer 54. This data line permits controller 23 to control the operation of multiplexer 54.

Figure 7A:
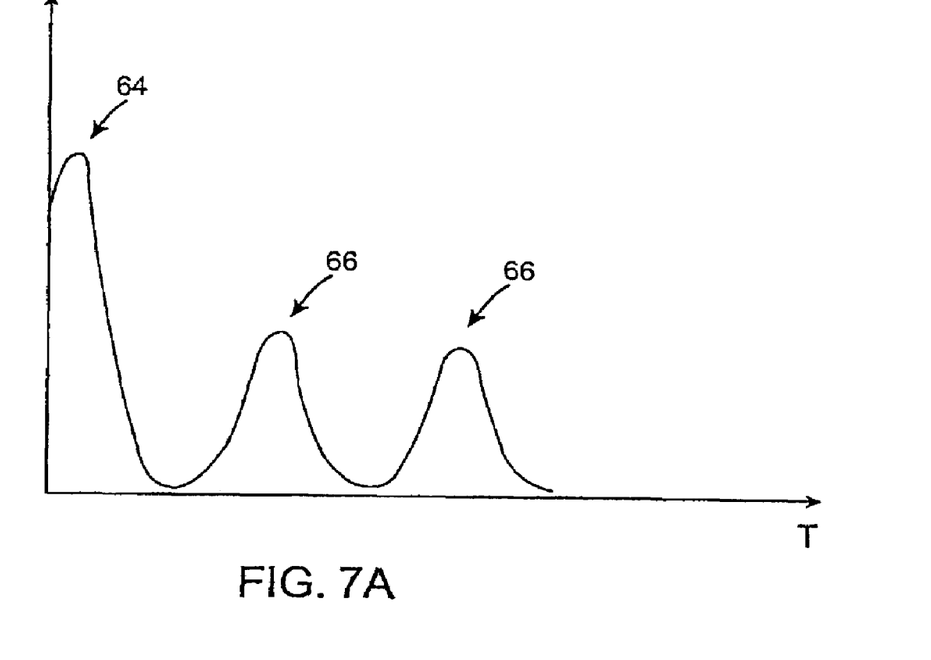
FIGS. 7A-7B depict energizing and reflected signals sent to and received by a transducer element of the present invention.
Figure 7B:
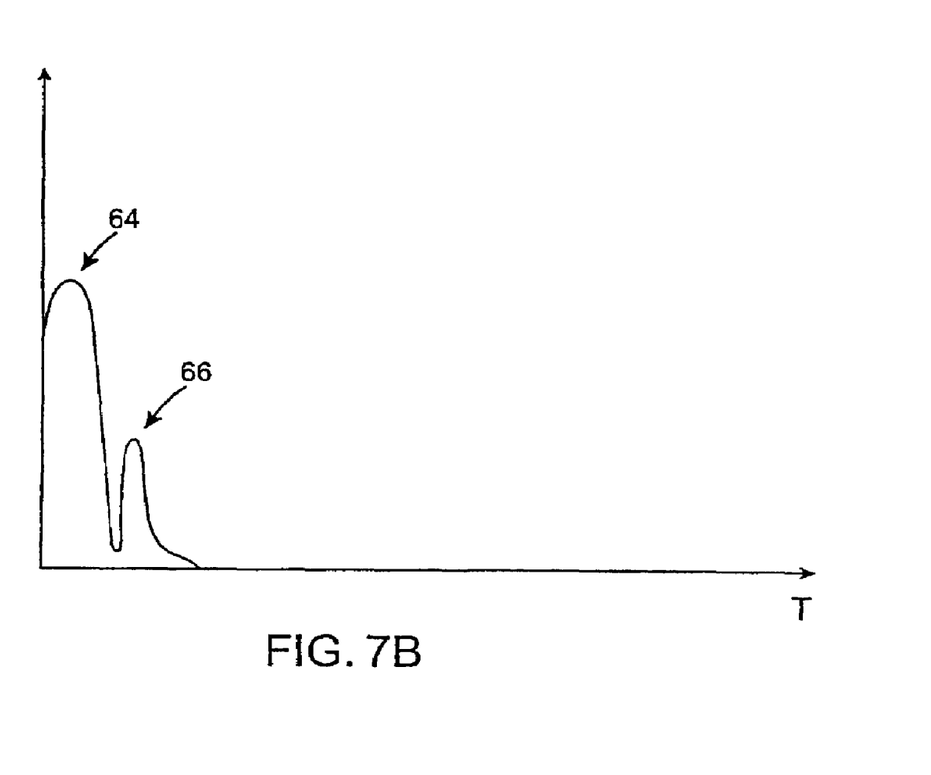
Figure 8:
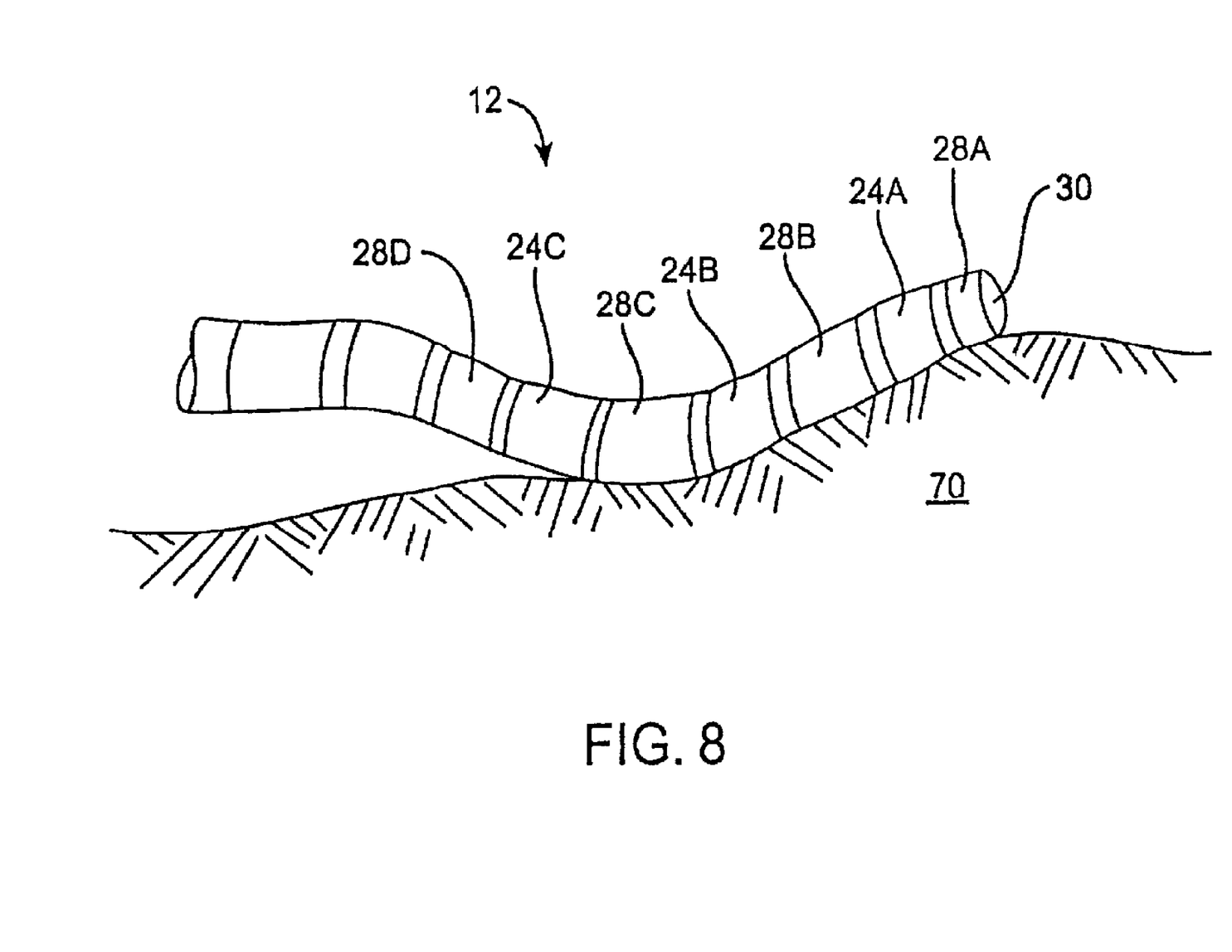
FIG. 8 depicts an embodiment of a medical catheter apparatus of the present invention in contact with tissue.

Turning now to FIGS. 7 and 8, the operation of medical catheter apparatus 2 and system 4 according to an embodiment of the present invention will be described. Medical catheter apparatus 2 operates by having transducer elements 28 detect the proximity of a tissue 70 with respect to elongate body 12 distal end 10. Controller 23 calculates the time delay between transducer element 28 excitation and the receipt of a reflected signal 66 from surrounding tissue 70 to determine the distance between transducer element 28 and tissue 70, as further described below.

As shown by FIGS. 7A and 7B, an excitation signal 64 is transmitted from controller 23 to transducer elements 28, or to multiplexer 54 for transmission to transducer elements 28. Excitation signal 64 is converted by transducer 28 into an ultrasound signal which propagates out into surrounding fluid and tissues within the patient. Transducer elements 28 detect reflected signals 66 and transfer electrical representations of those signals to controller 23 for processing.

Controller 23 uses the time delay between the excitation 64 and the receipt of reflected signal 66 to calculate the approximate distance to the reflecting object. Controller 23 is capable of differentiating between low amplitude blood reflections and larger amplitude tissue reflections 66 as shown in FIG. 7. Controller 23 further differentiates from a randomized back scatter versus more stable tissue scatter. The distance from each transducer 28 to tissue 70 may be calculated by knowing the speed of sound and measuring the time response to the larger amplitude tissue reflections. If the signal completely consists of larger amplitude wave forms, intimate contact will be diagnosed. While transducers 28 inherently have a blind zone/time period in which signals cannot be measured, the resulting blind zone distance is rather small. For example, for a 30 Mhz transducer, this distance is approximately 0.15 mm. Hence, reflected signal 66 measured almost immediately after excitation 64 occurs results in the distance from the transducer 28 to tissue 70 being less than about 0.15 mm blind distance.

Medical catheter system 4, therefore, can be operated by inserting apparatus 2 into the patient and positioning distal end 10 of apparatus 2 near a desired location of the patient's anatomy. Transducer elements 28 are energized with excitation signal 64 and reflected signals 66 are received and processed by controller 23. Controller 23 determines whether or not transducer elements 28 are in contact with tissue 70. If at least one transducer element 28 is in contact with tissue 70, ablation using an adjacent ablation element 24 may occur. Preferably, as shown in FIG. 8, it will be desirable to have more than one transducer element 28 in contact with tissue 70.

Controller 23 can be operated in a variety of ways to determine the number and positioning of transducer elements 28 which may be in contact with tissue 70. For example, as shown in FIG. 8, transducer elements 28A, 28B and 28C would indicate that they were in contact with tissue 70. This may permit the physician to ablate tissue 70 using electrode 24A and electrode 24B. Transducer element 28D would not indicate contact with tissue 70. Therefore, it is inconclusive whether ablation element 24C is in contact with tissue 70. Hence, the physician may choose not to ablate with ablation element 24C.

In one embodiment, controller 23 may use a green and red light system for indicating when transducer elements 28 are in contact with tissue 70. In one particular embodiment, for example, controller 23 has a red light and a green light for each transducer element 28A-28D depicted in FIG. 8. The green light would be illuminated by controller 23 when the corresponding transducer element 28 is in contact with tissue 70. Red lights would be illuminated for those transducer elements 28 not in tissue contact.

Alternatively, a single green and red light may be used for apparatus 2, whereby the green light is illuminated by controller 23 only when all transducer elements 28 are in tissue contact. Still another embodiment involves several transducer elements 28 corresponding to a single green/red light set. For example, elements 28A and 28B may have one green light which controller 23 illuminates when both elements 28A and 28B are in tissue contact. The red light corresponding to elements 28A and 28B would be illuminated if one or both transducer elements 28A and 28B are not in contact with tissue 70. It will be appreciated by those skilled in the art that there exist numerous ways within the scope of the present invention for controller 23 to indicate when tissue 70 contact has been achieved by transducer elements 28, including audible tones and the like.

Ablation elements 24 are preferably used for mono-polar ablation, although bi-polar ablation also is anticipated within the scope of the present invention. Ablation elements 24 preferably comprise electrodes. In this manner, RF ablation may occur using ablation elements 24.

Alternatively, ablation elements 24 may comprise ablation ultrasound transducers. In this manner, transducer elements 28 are operated in pulse mode to determine their distance from tissue 70. Upon tissue contact, ablation transducers 24 would be used to ablate tissue 70. The use of transducers for acoustic ablation is further described in U.S. Pat. No. 5,630,837, the complete disclosure of which has been previously incorporated herein by reference.

Alternatively, transducer elements 28 can be used to both image and ablate tissue 70. Transducer elements 28 would first be operated in pulse mode, to determine whether transducer elements 28 are in contact with tissue 70. Transducer elements 28 then would receive a continuous wave or gated continuous wave electrical signal having a frequency of about 10-15 MHz, and transducer elements 28 would ablate tissue 70 using ultrasound ablation.

Figure 9:
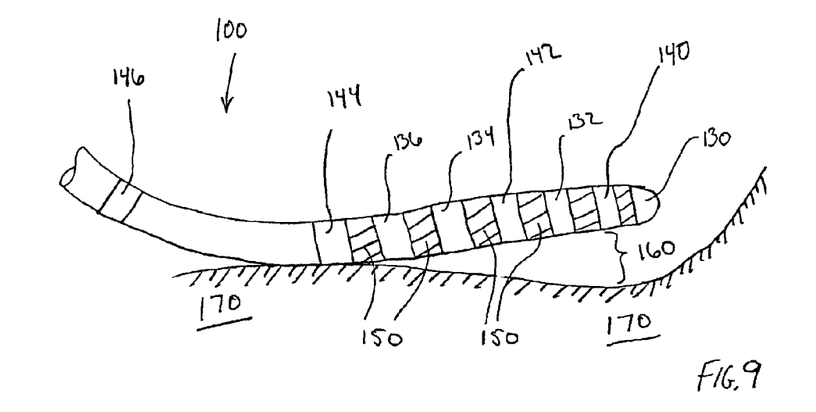
FIG. 9 is an overall view of a medical catheter according to an alternative embodiment of the present invention.
Figure 10:
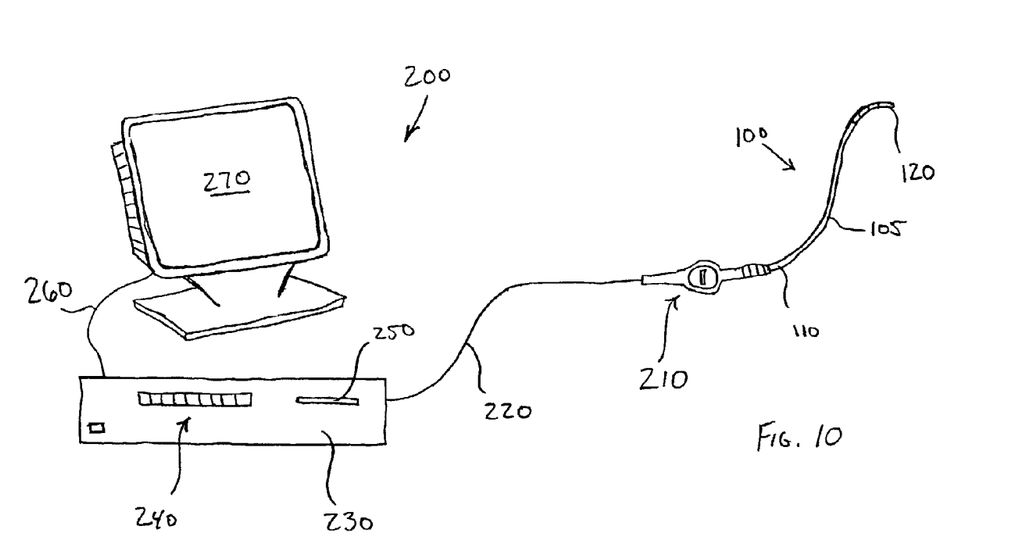
FIG. 10 is a simplified overall view of a medical catheter system according to an embodiment of the present invention.

Turning now to FIGS. 9 and 10, an alternative embodiment of a medical catheter 100, and a medical catheter system 200 according to the present invention will be described. Medical catheter 100 includes an elongate body 105 having a proximal end 110 and a distal end 120. Proximal end 110 is coupled to a steering device 210 as shown in FIG. 10. Steering device 210 may, but need not be similar to that described in conjunction with FIG. 1. The length of catheter 100 may vary within the scope of the present invention. In one embodiment, the length of catheter 100 is sufficient to permit insertion into the femoral vein in a patient leg and traverse through the patient vasculature to reach the heart muscle or other region to be treated. Distal end 120, as best shown in FIG. 9, includes a plurality of elements coupled to or otherwise disposed therewith for tissue mapping, tissue orientation detection, tissue imaging, tissue treatment, and the like. In the embodiment shown in FIG. 9, distal end 120 includes a tip electrode 130 disposed at or near the distal tip of catheter 100. In one embodiment, tip electrode 130 provides an exemplary electrode for ablation treatments as previously described.

Catheter 100 includes a plurality of spaced apart electrodes 132, 134, and 136 coupled to distal end 120. In one embodiment, electrodes 132-136 comprise ring electrodes. In a particular embodiment, ring electrodes 134 and 136 operate as an electrode pair for a tissue mapping function. Further, electrodes 130 and 132 may operate as an electrode pair for a tissue mapping function. Catheter 100 further includes a plurality of tissue orientation detectors 140, 142, 144, and 146 spaced along elongate body 105. As shown in FIG. 9, tissue orientation detector 140 is disposed near the distal tip of elongate body 105 such that detector 140 is in close proximity to tip electrode 130. Similarly, detector 146 is disposed proximal to the remaining elements of distal end 120, and may be used for orientating or detecting the location of distal end 120.

Distal end 120 further includes a plurality of insulators 150. Insulators 150 are adapted to insulate electrodes 130-136 from one another, and/or to insulate detectors 140-146 from one another, and/or to insulate detectors 140-146 from electrodes 130-136. In a particular embodiment, each electrode 130-136 has at least one detector 140-146 disposed adjacent thereto, with possibly an intervening insulator 150 therebetween. For example, tip electrode 130 has detector 140 located proximal thereto. Electrode 132 has detector 140 located distal thereto, and detector 142 located proximal thereto. While electrodes 134 and 136 are separated from one another by only an insulator 150, each electrode 134 and 136 has an adjacent detector 142 and 144, respectively. In this manner, detectors 140-146 and electrodes 130-136 may be used in concert for a variety of procedures as further described herein. It will be appreciated by those skilled in the art that the orientation and order of the various detectors 140-146, electrodes 130-136 and insulators 150 may vary within the scope of the present invention.

In one embodiment, tissue orientation detectors 140-146 include transducers. Transducers 140-146 may be adapted to transduce between a variety of physical parameters. For example, in one embodiment, at least some transducers 140-146 are adapted to transduce between ultrasound energy and a voltage. This may occur, for example, when one or more of detectors 140-146 comprise ultrasound transducers which are adapted to transmit an ultrasound energy wave when a voltage is applied across opposing surfaces of the detector 140-146. The ultrasound wave travels towards a tissue 170, and is reflected by tissue 170. The reflected wave is received by detector 140-146, and is converted into a voltage by detector 140-146. The voltage is transmitted to a controller 230, such as is shown in FIG. 10. In this manner, detectors 140-146 transduce between ultrasound energy and voltage. Alternatively, detectors 140-146 may be adapted to transducer between a voltage and a magnetic field. For example, a magnetic or electromagnetic field generator can be placed in proximity to the patient. In one embodiment, the catheter carries one or more transducers that detect the magnetic or electromagnetic field and convert it into a voltage. The voltage is then supplied to controller 230 for orientation detection purposes. Alternatively, other transducer types may be used, including electrical transducers, permanent magnets, optical transducers, and the like.

Medical catheter 100 is adapted to perform one or more functions, and may be adapted to image tissue, map tissue, assist in orienting itself with respect to tissue, treat tissue, and the like. For example, catheter 100 may be adapted for mapping a patient tissue, such as heart tissue. This may occur a number of ways within the scope of the present invention. For example, tissue orientation detectors 140-146 may be used by inserting catheter 100 into a patient's vasculature and transferring distal end 120 to a desired region of the patient. Catheter 100 then may be used in conjunction with one or more reference catheters to perform a three-dimensional localization process to help map the general shape of the patient's tissue, such as the heart muscle. Details of a three-dimensional localization process are further described in U.S. Pat. No. 6,490,474, entitled "System and Method for Electrode Localization Using Ultrasound," the complete disclosure of which is incorporated herein by reference for all purposes.

In an alternative embodiment, catheter 100 is used to map the electrical activity of tissue 170. For example, in one embodiment, catheter 100 is inserted into a desired region of the patient, and positioned such that one or more electrodes 130-136 are in contact with tissue 170. Tissue mapping procedures may then be performed to map the electrical activity of the heart muscle. Such electrode mapping techniques are further described in U.S. Pat. No. 5,598,848, entitled "Systems and Methods for Positioning Multiple Electrode Structures in Electrical Contact with the Myocardium"; U.S. Pat. No. 5,487,391, entitled "Systems and Methods for Deriving and Displaying the Propagation Velocities of Electrical Events in the Heart"; and U.S. Pat. No. 6,516,807, entitled "System and Methods for Locating and Guiding Operative Elements within Interior Body Regions," the complete disclosures of which are incorporated herein by reference for all purposes.

While the above-noted references discuss the use of a basket catheter for placing electrodes in contact with heart tissue to be mapped, the present invention may be adapted to insure tissue contact prior to mapping. For example, the techniques discussed in conjunction with FIGS. 1-8 may be used, including the time delay of ultrasound signals transmitted by, and subsequently received by detectors 140-146, to verify tissue contact.

In an alternative embodiment, catheter 100 maps the electrical activity of tissue 170 using a non-contact mapping technique. Non-contact mapping uses electrodes 130-136 to sense electrical activity within tissue 170 notwithstanding the fact there may be a gap 160 between electrode(s) 130-136 and tissue 170. These far field signals received by electrodes 130-136 are mapped onto the surface of tissue 170 using an algorithm which takes into account the relationship between distal end 120 and tissue 170, and the general orientation of catheter 100 with respect to tissue 170. In this manner, electrically active tissue 170 is mapped. Additional details on mapping tissue, including non-contact mapping, may be found in U.S. Pat. No. 6,240,307 entitled "Endocardial Mapping System," the complete disclosure of which is incorporated herein by reference.

Data received or generated by detectors 140-146, and/or electrodes 130-136 may be optionally transmitted to controller 230 by coupling catheter 100 to controller 230 using a cable 220 or other electrically conductive medium. In one embodiment, controller 230 comprises a microprocessor coupled to a computer readable storage medium having software or other programs adapted to perform a variety of procedures. Controller 230 may include an input device 250 for receipt of a compact disc, a DVD, or the like containing reference data, algorithms or related processing software, or the like. In a particular embodiment, controller 230 further includes a light array 240 that is adapted to visually indicate to the operator or physician when one or more detectors 140-146 are in contact with tissue 170. As previously described, light array 240 may comprise a green/red light system, and/or may include some other visual or audio indicator. In one embodiment, controller 230 includes a digitizer that is adapted to digitize the data received from catheter 100 and display an image of tissue 170 on a monitor 270. Controller 230 may be coupled to monitor 270 using a cable 260 or the like. Alternatively, wireless connections may be used to couple controller 230 with display 270 and/or to couple controller 230 with catheter 100.

Figure 11:
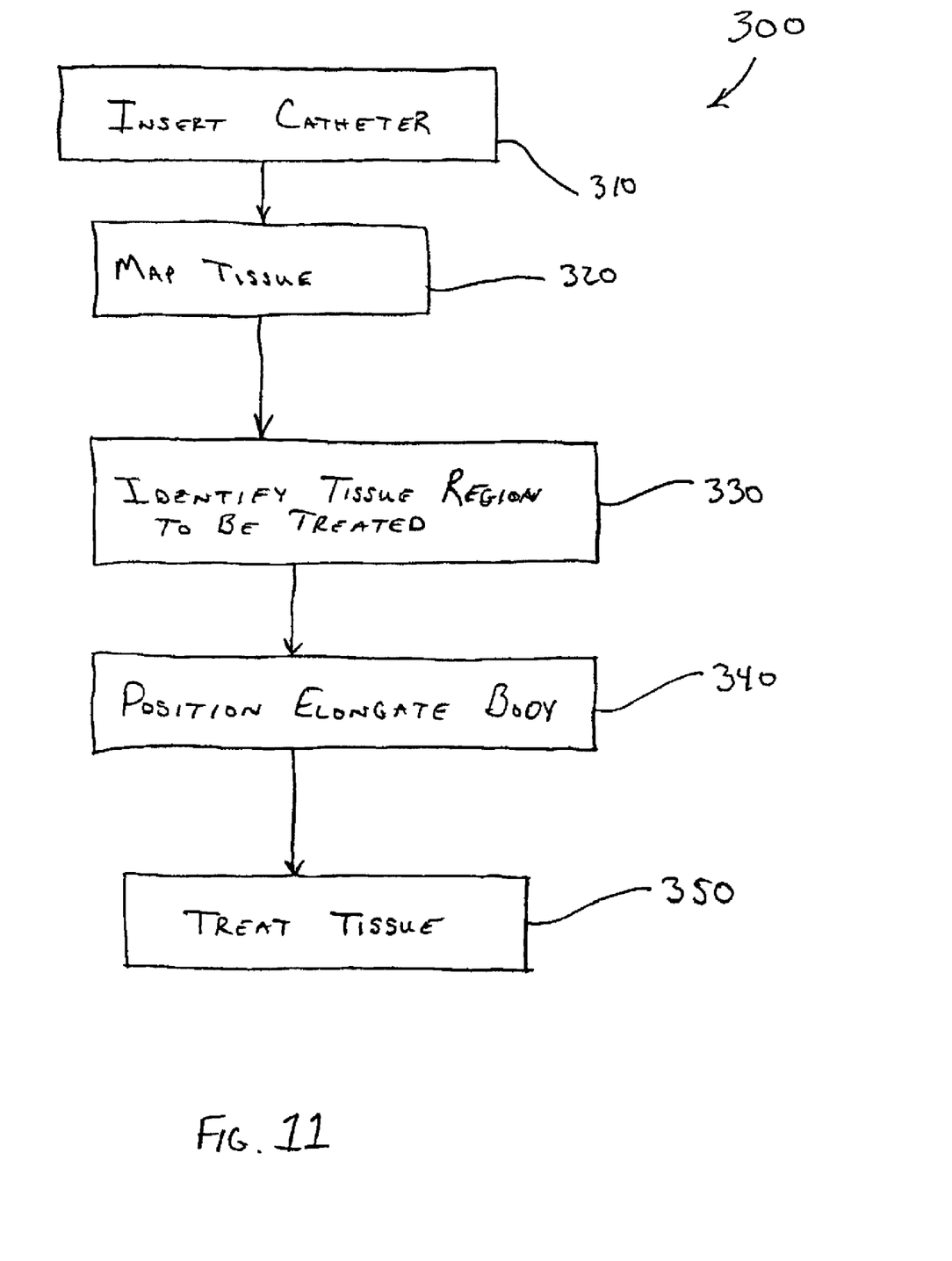
FIG. 11 is a simplified flow chart of a method of the present invention.

Turning now to FIG. 11, an embodiment of a method 300 of precisely positioning catheter 100 according to the present invention will be described. Method 300 includes inserting catheter 100 into a patient (block 310). As previously described, this may occur, for example, by inserting catheter 100 through the femoral vein of the patient. Catheter 100 is then used to map tissue (block 320). The mapping of tissue 170 may include three-dimensional localization techniques, and/or the mapping of electrical activity within tissue 170, both as previously described. Method 300 further includes identifying a tissue region to be treated (block 330). This may occur, for example, by displaying an image of tissue 170 on display 270 for review by a physician or other operator of system 200.

Method 300 further includes positioning of elongate body 105 (block 340). This may involve the various procedures as previously described, and may include the use of detectors 140-146 to orient catheter 100 within the desired region of the patient. For example, detectors 140-146 may be used to generally determine that distal end 120 is in the proper region of the patient. Further, the positioning of catheter 100 may include using one or more detectors 140-146 to determine that tissue 170 has been contacted. In another embodiment, electrodes 130-136 are used to facilitate orientation of catheter 100. This may occur, for example, by receiving electrical signals from the heart and comparing the electrical signals with a previously generated map of electrical signals of tissue 170, such as that received as a result of the mapping of tissue in block 320. The comparison may assist in determining the orientation of catheter 100 relative to tissue 170.

Once catheter 100 has been precisely positioned, or if non-contact techniques are employed once a cardiac map has been obtained, the physician or operator of system 200 may optionally treat tissue 170 (block 350). As previously discussed, one such treatment involves the ablation of tissue 170, or a portion of tissue 170, such as may be desired to treat atrial fibrillation. The treatment aspects of method 300 may further include the delivery of medicines or other therapy to tissue 170 instead of ablation. It will be appreciated by those skilled in the art that while method 300 is depicted and described as including a series of processes, the procedures identified in FIG. 11 may occur in an order different than that shown. For example, the physician may have already identified a tissue region to be treated. In this case, block 330 may be removed from method 300. Further, the positioning of elongate body in block 340 may occur prior to tissue mapping, and/or after tissue treatment.

Figure 12A:
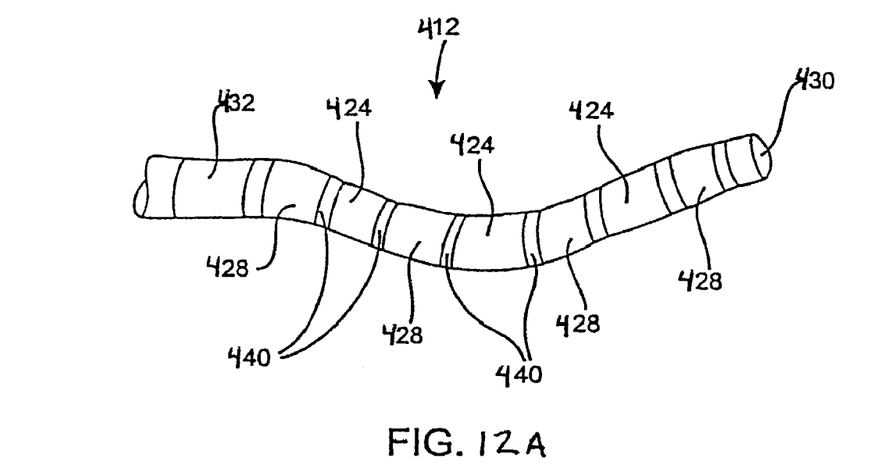
FIGS. 12A and 12B depict a simplified overall view and a cross-sectional side view of an alternative embodiment of a catheter according to the present invention.
Figure 12B:
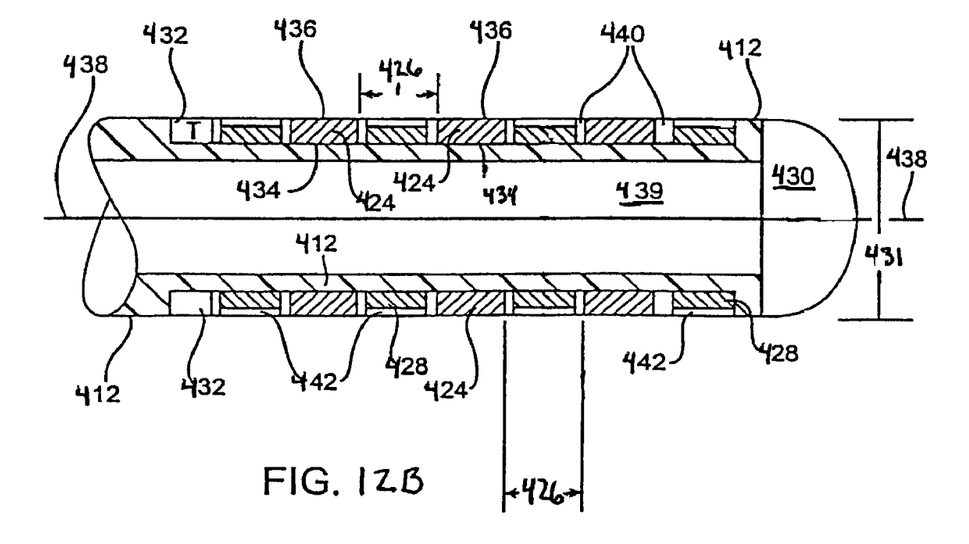

An alternative embodiment of a medical catheter according to the present invention will be described in conjunction with FIGS. 12A and 12B. As shown, the catheter includes an elongate body 412 having a working lumen 439 and a longitudinal axis 438. A plurality of spaced-apart electrodes 424 are disposed on body 412. Interspaced amongst electrodes 424 are a plurality of tissue orientation detectors 428. In one embodiment, tissue orientation detectors 428 include transducer elements 428. For embodiments in which orientation detectors 428 comprise transducers, and in particularly ultrasound transducers, detectors 428 may include one or more matching layers 442 operably attached to the outer face 446 of at least some of the detectors 428. Matching layers 442 operate to improve transducer 428 performance. Detectors 428 also may operate without matching layers 442 within the scope of the present invention. Further, while shown coupled to elongate body 412 in an alternating fashion, the arrangement of electrodes 424 and detectors 428 may vary within the scope of the present invention.

Detectors 428 have an outer diameter, which may be less than an outer diameter 431 of flexible elongate body 412 or, alternatively, about equal to diameter 431. Preferably, diameter 431 of body 412 is less than about eight (8) French to permit the introduction of the medical catheter into a patient's tortuous vasculature. A plurality of gaps 426 separate electrodes 424 and detectors 428 from each other and/or from one another. Each gap 426 need not contain detector 428, and gaps 426 may contain more than one detector 428 within the scope of the present invention. A plurality of insulators 440 are disposed between at least some orientation detectors 428 and/or electrodes 424. Insulators 440 may comprise polyimide, polyesters, teflon or the like to insulate adjoining detectors 428 and/or electrodes 424.

In one embodiment, a temperature sensor 430 is disposed at or near the distal end of body 412, and a proximal temperature sensor 432 is disposed proximal to electrodes 424. Temperature sensors 430 and 432 may comprise thermocouples, thermistors or the like within the scope of the present invention. In an alternative embodiment, temperature sensor 432 is replaced with a tip electrode. In this manner, the distal tip of elongate body 412 may be used for mapping and/or ablation procedures.

In one embodiment, electrodes 424 are adapted for a tissue mapping function. In a particular embodiment, electrodes 424 are adapted for only a tissue mapping function, and may be sized accordingly. For example, electrodes 424 may comprise ring electrodes. In such an embodiment, electrodes 424 may have a smaller exposed outer surface 436 than similar ablation electrodes. In a particular embodiment, electrodes 424 further include an inner surface 434, which facilitates electrical coupling to a controller by having a wire or wires (not shown) extending through lumen 439. In this manner, the catheter of FIGS. 12A and 12B is adapted for tissue mapping and tissue orientation functions, and optionally, tissue ablation. Tissue imaging also may be included.

The invention has now been described in detail. However, it will be appreciated that certain changes and modifications may be made. For example, while FIGS. 2, 3, 5 and 8 depict transducer elements 28 interspaced between all ablation elements 24, transducers 28 may only exist between some of ablation elements 24 and in some gaps 26. Therefore, the scope and content of this invention are not limited by the foregoing description. Rather, the scope and content are to be defined by the following claims.

What is claimed is:

1. A medical catheter, comprising:
   a flexible elongate body having a proximal end and a distal end;
   a plurality of transducers operably attached to the flexible body near the distal end;

a multiplexer disposed within the flexible elongate body near the distal end and coupled to the plurality of transducers; and a transmission line coupled to the multiplexer, the transmission line extending from the multiplexer to the proximal end of the flexible elongate body;

wherein the multiplexer is adapted to receive a series of excitation pulses and a clock signal from the transmission line and to direct each one of the excitation pulses to one of the transducers based on the received clock signal.

2. The medical catheter of claim 1, wherein the multiplexer is adapted to direct the series of excitation pulses to the transducers such that the transducers are excited in a sequence.

3. The medical catheter of claim 1, further comprising a plurality of spaced apart electrodes operably attached to the flexible body near the distal end.

4. The medical catheter of claim 1, wherein at least some of the transducers comprise ultrasound transducers.

5. The medical catheter of claim 1, wherein at least some of the transducers comprise electric, magnetic or electromagnetic transducers.

6. The medical catheter of claim 1, wherein at least one of the transducers is adapted to both image and ablate tissue.

7. The medical catheter system of claim 6, wherein the at least one of the transducers adapted to both image and ablate tissues is adapted to ablate tissues when receiving a continuous wave or gated continuous wave electrical signal having a frequency of about 10-15 MHz.

8. A medical catheter, comprising:
a flexible elongate body having a proximal end and a distal end;
a plurality of transducers operably attached to the flexible body near the distal end;
a multiplexer disposed within the flexible elongate body near the distal end and coupled to the plurality of transducers; and
a transmission line coupled to the multiplexer, the transmission line extending from the multiplexer to the proximal end of the flexible elongate body;
wherein the multiplexer includes a counter adapted to count a number of excitation pulses on the transmission line, and the multiplexer is adapted to coordinate a transfer of excitation pulses from the transmission line to the transducers based on the count of the counter.

9. A medical catheter system, comprising:
a medical catheter comprising:
a flexible elongate body having a proximal end and a distal end;
a plurality of transducers operably attached to the flexible elongate body near the distal end;
a multiplexer disposed within the flexible elongate body near the distal end and coupled to the plurality of transducers; and
a transmission line coupled to the multiplexer, the transmission line extending from the multiplexer to the proximal end of the flexible elongate body;
a controller coupled to the transmission line;
wherein the multiplexer is adapted to receive a series of excitation pulses and a clock signal from the controller via the transmission line and to direct each one of the excitation pulses to one of the transducers based on the received clock signal.

10. The medical catheter system of claim 9, further comprising a data line coupled between the multiplexer and the controller, and the controller is adapted to control operation of the multiplexer through the data line.

11. The medical catheter system of claim 9, further comprising a plurality of spaced apart electrodes operably attached to the flexible elongate body near the distal end.

12. The medical catheter system of claim 11, wherein the controller is adapted to determine whether one of the transducers is in contact with a tissue and to activate one of the electrodes to ablate the tissue when the controller determines that the transducer is in contact with the tissue.

13. The medical catheter system of claim 9, wherein at least some of the transducers comprise ultrasound transducers.

14. The medical catheter system of claim 9, wherein at least some of the transducers comprise electric, magnetic or electromagnetic transducers.

15. The medical catheter system of claim 9, wherein at least one of the transducers is adapted to both image and ablate tissue.

16. The medical catheter system of claim 15, wherein the controller is adapted to determine whether the at least one of the transducers adapted to both image and ablate tissue is in contact with a tissue and to activate the at least one transducer to ablate the tissue when the controller determines that the at least one transducer is in contact with the tissue.

17. A medical catheter system, comprising:
a medical catheter comprising:
a flexible elongate body having a proximal end and a distal end;
a plurality of transducers operably attached to the flexible elongate body near the distal end;
a multiplexer disposed within the flexible elongate body near the distal end and coupled to the plurality of transducers; and
a transmission line coupled to the multiplexer, the transmission line extending from the multiplexer to the proximal end of the flexible elongate body;
a controller coupled to the transmission line;
wherein the multiplexer includes a counter adapted to count a number of excitation pulses on the transmission line, and the multiplexer is adapted to coordinate a transfer of excitation pulses from the transmission line to the transducers based on the count of the counter.

* * * * *